US008853187B2

(12) United States Patent
Zanetti et al.

(10) Patent No.: US 8,853,187 B2
(45) Date of Patent: *Oct. 7, 2014

(54) COMPOSITION COMPRISING BISPHOSPHONATES FOR PREVENTION AND/OR TREATMENT OF METABOLIC DISEASES OF BONES, PROCESS FOR PREPARING SUCH COMPOSITION AND USE THEREOF

(75) Inventors: Daniel Zanetti, Buenos Aires (AR); Damian Cairatti, Buenos Aires (AR); Enrique Piccinni, Buenos Aires (AR); Emilio J. A. Roldan, Buenos Aires (AR); Socrates Papapoulos, AA Leiden (NL)

(73) Assignees: Gador S.A., Buenos Aires (AR); University of Leiden, AA Leiden (NL)

( * ) Notice: Subject to any disclaimer, the term of this patent is extended or adjusted under 35 U.S.C. 154(b) by 505 days.

This patent is subject to a terminal disclaimer.

(21) Appl. No.: 12/480,086

(22) Filed: Jun. 8, 2009

(65) Prior Publication Data

US 2009/0247491 A1 Oct. 1, 2009

Related U.S. Application Data

(63) Continuation of application No. 10/466,897, filed as application No. PCT/EP01/00690 on Jan. 23, 2001, now Pat. No. 7,560,490.

(51) Int. Cl.
*A61K 31/663* (2006.01)
*C07F 9/38* (2006.01)
*A61K 9/00* (2006.01)

(52) U.S. Cl.
CPC .............. *A61K 9/0095* (2013.01); *A61K 31/663* (2013.01); *C07F 9/3856* (2013.01); *C07F 9/3839* (2013.01); *C07F 9/38* (2013.01); *C07F 9/3873* (2013.01); *C07F 9/3843* (2013.01); *C07F 9/386* (2013.01)
USPC ........................................... 514/108; 562/21

(58) Field of Classification Search
None
See application file for complete search history.

(56) References Cited

U.S. PATENT DOCUMENTS

| | | | | |
|---|---|---|---|---|
| 4,313,765 A * | 2/1982 | Baird et al. | .................. | 106/162.8 |
| 4,788,220 A | 11/1988 | Mody et al. | | |
| 5,344,825 A | 9/1994 | Khanna et al. | | |
| 5,438,048 A | 8/1995 | Nikander et al. | | |
| 5,462,932 A | 10/1995 | Brenner et al. | | |
| 5,518,711 A | 5/1996 | Tonariya et al. | | |
| 5,674,522 A * | 10/1997 | Shah et al. | ..................... | 424/439 |
| 5,688,529 A | 11/1997 | Lidgate et al. | | |
| 5,780,046 A | 7/1998 | Humber et al. | | |
| 6,555,544 B2 | 4/2003 | Francois et al. | | |
| 6,750,241 B2 * | 6/2004 | Griffin et al. | .................. | 514/414 |
| 7,560,490 B2 * | 7/2009 | Zanetti et al. | .................. | 514/578 |
| 2001/0051636 A1 | 12/2001 | Black et al. | | |

FOREIGN PATENT DOCUMENTS

| | | |
|---|---|---|
| EP | 1188441 A1 | 3/2002 |
| JP | 1258618 A | 10/1989 |
| JP | 69408 T | 1/1994 |
| JP | 6116170 A | 4/1994 |
| JP | 6504045 T | 5/1994 |
| JP | 840911 T | 2/1996 |
| JP | 8333245 A | 12/1996 |
| JP | 92949 T | 1/1997 |
| JP | 9504525 T | 5/1997 |
| JP | 9509648 T | 9/1997 |
| JP | 10504020 T | 4/1998 |
| JP | 11502506 T | 3/1999 |
| WO | 9511029 A1 | 4/1995 |
| WO | 9619998 A1 | 7/1996 |
| WO | 9814196 A1 | 4/1998 |
| WO | 9925354 A2 | 5/1999 |
| WO | 0049037 A1 | 8/2000 |
| WO | 0074685 A1 | 12/2000 |
| WO | WO02/049451 * | 6/2002 ............ A23L 1/0534 |

OTHER PUBLICATIONS

Pelger et al., "Effects of the Bisphosphonate Olpadronate in Patients With Carcinoma of the Prostate Metastatic to the Skeleton" Bone (1998) vol. 22 No. 4, pp. 403-408.*
Maccagno et al., "Double Blind Radiological Assessment of Continuous Oral Pamidronic Acid in Patients with Rheumatoid Arthritis" Scandinavian Rhematology Research Foundation (1994) pp. 211-213.*
Jain et al., "Polymorphism in Pharmacy" Indian Drugs (1986) vol. 23 No. 6 pp. 315-329.*
Lieberman et al., "Pharmaceutical Dosage Forms" published 1990 by Marcel Dekker et al., vol. 2, pp. 462-472.*
Vippaguinta et al. "Crystalline SOlids" Advanced Drug Delivery Reviews (2001) vol. 48 pp. 3-26.*
Braga et al., "Making Crystals from Crystals: a green route to crystal engineering and polymorphism" ChemComm (2005) pp. 3635-3645.*
Iyakuhin-Tenkabutsu Jiten (dictionary of pharmaceutical additives), Japan, Yakuji Nippo Limited., Jan. 14, 1994, pp. 31-32, 36-37, 49-50, 57 and 78.
2. Guide Book of the Japanese Pharmacopoeia 13th Edition, General Notices, General Rules for Preparations, General Tests, Japan, Feb. 19, 1999, p. A-105.
Susan Budavari, et al., The Merck Index, Twelfth Edition, 1996, Published by Merck Research Laboratories Division of Merck & Co., Inc. , Whitehouse Station, NJ, pp. 454-455.

\* cited by examiner

*Primary Examiner* — Eric Olson
(74) *Attorney, Agent, or Firm* — Patent Central LLC; Stephan A. Pendorf

(57) ABSTRACT

The present invention relates to a composition for prevention and/or treatment of metabolic diseases of bones comprising at least one bisphosphonate; viscosity agents comprising carboxymethylcellulose and xanthan gum; at least one flavoring agent; and purified water; a process for preparing a composition according to the present invention; and use of such a composition for prevention, treatment and/or diagnosis of metabolic diseases of bones, especially for children.

19 Claims, No Drawings

COMPOSITION COMPRISING BISPHOSPHONATES FOR PREVENTION AND/OR TREATMENT OF METABOLIC DISEASES OF BONES, PROCESS FOR PREPARING SUCH COMPOSITION AND USE THEREOF

This application is a continuation of U.S. application Ser. No. 10/466,897, now U.S. Pat. No. 7,560,490, filed Dec. 12, 2003, which is a national stage application of PCT/EP01/00690, filed Jan. 23, 2001.

FIELD OF THE INVENTION

The present invention relates to a composition for prevention and/or treatment of metabolic diseases of bones, a process for preparing such composition and use thereof.

BACKGROUND OF THE INVENTION

Bisphosphonates are well known chemical compounds used in medicine for the prevention or treatment of several metabolic diseases of the bone, e.g. metabolic osteopathies, such as osteoporosis, cancer metastasis and the osteopathies associated with rheumatoid arthritis.

Bisphosphonates can be prepared using various methods already described in the literature through which different crystalline species can be obtained. A selection of known bisphosphonates is presented in the following scheme.

Scheme Chemical structure of some bisphosphonates and amino-bisphosphonic acids

A)
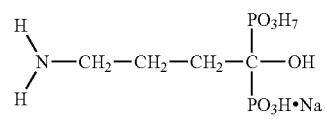
Monosodic alendronate

B)
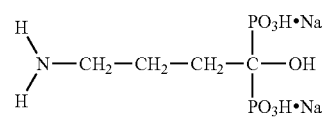
Disodic pamidronate

C)
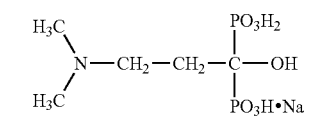
Monosodic olpadronate

D)
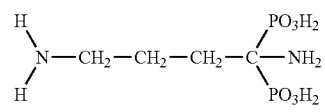
Amino-alendronic acid

E)
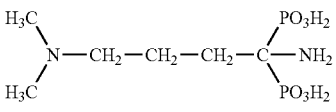
Dimethyl-amino-alendronic acid

F)
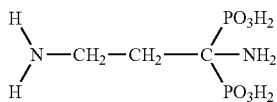
Amino-pamidronic acid

G)
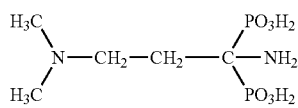
Amino-olpadronic acid

H)
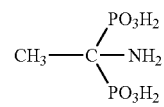
Amino-etidronic acid

Bisphosphonates may exist in the form of acids, salts, hydrates and amino-derivatives.

Monosodium alendronate, for example, may be prepared according to the Argentinean Patent AR 000.052.

Pamidronate and olpadronate are other bisphosphonic derivatives which contain one nitrogen in the lateral chain. Olpadronate is the naturally most soluble compound in the group of bisphosphonates and may be synthesized according to the Argentinean Patent AR 246.743 and EP 0 891979 AI, whereas the synthesis of pamidronate is disclosed in the Argentinean Patent AR 218.558.

The amino-derivatives of bisphosphonates may be synthesised according to the methods stated in WO 97/02827 and AR 004.625.

Further synthetic routes to obtain pamidronate are disclosed in U.S. Pat. No. 3,962,432, further describing tablets, capsules, tooth-pastes and mouthwash containing pamidronate. U.S. Pat. No. 4,407,761 and U.S. Pat. No. 4,639,338 claim certain crystalline forms of pamidronate suitable for injectable solutions or pills, tablets, capsules and suppositories.

U.S. Pat. No. 4,446,052 discloses aqueous gels of tricalcic pamidronate to be administered in capsules or tooth-pastes, aimed at dissolving calcareous deposits.

Alendronate is a derivative of bisphosphonates known since the 1970's and a method for its synthesis is for example disclosed in U.S. Pat. No. 4,621,077, further disclosing general formulations of capsules, effervescent granules and injectable solutions. EP 402152 refers to trihydrate alendronate.

U.S. Pat. No. 5,462,932 discloses specific liquid oral formulations containing alendronate for facilitating deglutition in people who have difficulties in swallowing. The formulations of U.S. Pat. No. 5,462,932 are based on the presence of EDTA as stabilising agent and/or the presence of citric acid as buffer agent. Special stabilizers were deemed to be essential in the formulations of bisphosphonates.

EP 336851 discloses tablets of several types of bisphosphonates that contain sodium laurylsulphate as excipient which is well known for persons skilled in the art. Other bisphosphonates, such as ibandronate, are described in U.S. Pat. Nos. 4,927,814 and 4,942,157.

Among the several medical indications presented by the bisphosphonates, the use in the prevention and treatment of established osteoporosis, see Papapoulos S. E. et al., The use of bisphosphonates in the treatment of osteoporosis, *Bone* 1992, 13: A41-A49A the treatment of bone metastases of cancer, see van Holten-Verzantvoort A. et. al., Oral pamidronate in the prevention and treatment of skeletal metastases in patients with breast cancer, *Medicina* (Buenos Aires), 1997, 57 (suppl.): 109-113; and the osteopathies associated with rheumatoid arthritis, see Maccagno A. et al., Double blind radiological assessment of continuous oral pamidronic acid in patients with rheumatoid arthritis, *Scan J Rheumatol*, 1994, 23:211-214, are highlighted.

All these medicinal uses imply the continuous/pulse administration of the bisphosphonate for long periods—5 or more years. Thus, the use of preparations suitable for oral administration is preferred.

"Continuous or pulse use" is understood as the use that fosters an inhibition of bone metabolism in a smooth and constant way, as proved by the steady levels curve of the markers of bone metabolism.

On the other hand, there is the non-continuous or cyclical use of bisphosphonates, stimulating a stronger depression of bone metabolism, followed by a tendency to cover basal level. With this modality, the biochemical markers curve thus fluctuates with troughs and peaks, demarcated by each cycle of administration.

In the continuous mode, each administration of bisphosphonates can be referred to as a pulse, see Roldan E J A et al, Clinical evaluation of bisphosphonates pharmacokinetics principles, *Medicine* (Buenos Aires), 1997, 57 (suppl.):76-82.

While daily, weekly of half-weekly pulses foster a continuous metabolic change in the bone, monthly, bimonthly or three-monthly pulses foster a metabolic discontinuous or cyclical change.

While no exact definition of the limit between cyclical and continuous modalities is known, the present invention is aimed at improving the pulse administration of bisphosphonates.

The "pulse" concept for bisphosphonate administration has also been common clinical practice in patient with small body mass, in children, and in those who do not tolerate daily administrations, see Roldan E J A et al, *J Pediat Endocrinol Metab* 1999, 12:555-559.

Up to now, however, the requirement of high doses of bisphosphonates has hindered a successful oral administration, especially due to potential problems of digestive tolerance. Moreover, most bisphosphonates have a very low solubility, 3% v/v or less. This favours a very low absorption of the compound, that means a bioavailability of at best 1%. Therefore, 99% of the remaining active substance may easily form lumps and precipitate in the digestive lumen which can result in digestive irritability. Symptoms resulting from such irritability may range from unspecified discomfort to pain, vomit and as well as esophagitis and gastritis.

Lesions in the digestive system can be related to the intrinsic potential of the dissolution of the pharmaceutical form and to the quantity of molecules administered each time, see Spivacow R. S. et al, Tolerability of oral bisphosphonates in patients with osteoporosis and other osteopathies, *Medicina* (Buenos Aires), 1997, 57(suppl.): 114-118.

Attempts have been made in the prior art to improve tolerability by prescribing doses low in bisphosphonates under very strict conditions, taking the bisphosphonate at least 30-60 minutes before breakfast with abundant water. Moreover, the patient must keep a strict fast and must remain standing or sitting during all the pre-breakfast period. Of course, these rigid instructions are bothersome and, together with side effects, may lead to the non-observance of the prescriptions. The patient finds little incentive to go on with an uncomfortable administration plan that disturbs the habitual rhythm of life and that, in most cases aims at preventing an uncertain fact, such as the probability of fractures due to osteoporosis in old age. Often, a short time after beginning treatment, the patient gives up the observation of the instructions and failures and side effects associated to poor fulfillment of the prescription appear.

Therefore, it is an object of the present invention to overcome the drawbacks of the prior art, especially to provide a composition for prevention, treatment and/or diagnosis of metabolic diseases of bones which would enable a more comfortable administration of bisphosphonates, in order to make possible a strict fulfillment of the prescriptions and long-term clinical effects. Moreover, it is a further object of the invention to lessen a risk factor of toxicity that is represented by the lumps resulting from the break-up of oral forms.

Moreover, it is a further object of the present invention to provide a process for preparing a composition according to the invention and to allow the use of such a composition for the prevention, treatment and/or diagnosis of metabolic diseases of bones.

SUMMARY OF THE INVENTION

The first objects are solved by a composition for prevention and/or treatment of metabolic diseases of bones comprising at least one bisphosphonate; viscosity agents comprising carboxymethylcellulose and xanthan gum; at least one flavouring agent; and purified water.

Preferably, the viscosity agents further comprise microcristalline cellulose.

Moreover, a composition is proposed wherein the bisphosphonate is present in an amount of between about 5 mg to about 600 mg, viscosity agents are present in an amount of between about 30 mg to about 1000 mg, the flavouring agent is present in an amount between about 150 mg to about 550 mg.

Preferably, the flavouring agent is a flavouring orange liquid.

DETAILED DESCRIPTION OF THE INVENTION

The composition may comprise the bisphosphonate in the form of its acid, salt, hydrate or amino-derivative.

Preferably, the bisphosphonate is selected from the group comprising monosodium alendronate, disodium pamidronate, monosodium olpadronate, amino-alendronate, amino-dimethyl alendronate, amino-parnidronate, amino-olpadronate, amino-etidronate, neridronate, etidronate, clodronate, ibanidronate, incadronate, risedronate, zolendronate, tiludronate and the like, and mixtures thereof.

The bisphosphonate may be soluble in the composition according to the present invention.

Preferably, sodium alendronate is present in the composition in an amount of between 5 mg to 140 mg. Alternatively, sodium olpedronate is present in an amount between of about 5 mg to about 500 mg, or disodium, pamidronate is present in an amount of between about 50 mg to about 600 mg.

According to the present invention, the composition may comprise further ingredients, such as sorbitol, glycerine, sodium saccharine, sodium cyclamate, methyl p-hydroxy benzoate, propyl p-hydroxybenzoate, sorbic acid, sucrose, and/or dyes.

Further, the present invention provides a process comprising the following steps:
(i) suspending carboxymethylcellulose in an appropriate solvent, such as sorbitol or glycerine;
(ii) dissolving bisphosphonate in demineralized water;

iii) heating further demineralized water to a temperature of about 60° C. and dissolving the potassium sorbate in water;
iv) suspending xanthan gum in the solution of step (iii);
v) dissolving sodium saccharine and sodium cyclamate in the mixture of step (iii);
vi) incorporating homogeneously the carboxymethylcellulose suspension of step (i) into the mixture of step (iii);
vii) adding to the mixture of step (vi) the bisphosphonate of step (ii);
viii) incorporating flavouring agent to the mixture of step (vii) once the temperature of the mixture is below 40° C.;
ix) reaching a desired volume with demineralized water; and
x) optionally fractionating the mixture of step (ix).

According to the present invention the composition may be used for prevention and/or treatment of metabolic diseases of bones, especially for metabolic osteopathies, cancer metastasis, osteopathies associated with rheumatoid arthritis, and osteoporosis.

Most preferably, the composition according to the invention may be used for a pulse administration.

Preferably the composition according to the present invention may be used for children.

The composition of the present invention may further be used as pre-breakfast pre-lunch and/or pre-dinner drink.

Surprisingly a composition was found for prevention and/or treatment of metabolic diseases of bones having natural-fruit-juice appearance, flavour and consistency. The excipients comprised in the composition do not cause any adverse interaction, keep the quantities given in soluble form, that is, minimise the risk of lumps or irritant particle formation, and of the subsequent contact with sensitive mucosa in patients that, incidentally, cannot remain upright. Because of their "nutritional" aspect, the composition is suitable and tasty enough to be administered as pre-breakfast juice, thus improving treatment completion, helping to keep in mind that it must be administered before breakfast or other meal, lessening side effects and consequently increasing the possibility of obtaining long-term therapeutic benefits.

These two latter concepts are based on the fact that in the composition according to the present invention all the given bisphosphonate is dissolved.

The composition according to the present invention may potentially be used in children.

Due to the fruit juice appearance of the composition of the present invention, it is simpler to remember when the composition according to the present invention should be taken, since it can be associated with a drink to be taken before meals, overcoming the therapeutic failure which often occurs when people forget to take the bisphosphonates or take them in the wrong moment.

However, it is also possible, for example for olpadronate, to administer the bisphosphonate together with food ad-libitum.

Moreover, it has to be mentioned that the composition of the present invention does not require any stabilizing agent, such as EDTA or citric acid. The composition of the present invention is stable in a glass or polymer container.

The fruit flavour of the composition of the present invention may be obtained by an orange essence, such as Meroar 73781, and a combination of carboxymethylcellulose, such as Avicel RC591 which is commercially available by F.M.C., and may comprise microcristalline cellulose, and xanthan gum. These synthetic excipients where neither used nor suggested before for a composition comprising bisphosphonates.

EMBODIMENTS OF THE INVENTION

The present invention will now be further illustrated by the following examples which are not intended to limit the scope of the invention in any way.

Example 1

Process for Preparing an Oral Solution of Bisphosphonate as Medicinal Fruit Juice A process for preparing a composition according to the present invention may comprise the following steps:

(i) suspending carboxymethylcellulose in glycerine or sorbitol;

(ii) dissolving bisphosphonate in an appropriate amount of demineralized water;

(iii) heating further demineralized water to a temperature of about 60° C. and dissolving the potassium sorbate in water;

(iv) suspending xanthan gum in the mixture of step (iii);

(v) dissolving sodium saccharine and sodium cyclamate in the mixture of step (iii);

(vi) incorporating homogeneously the carboxymethylcellulose suspension of step (i) into the mixture of step (iii);

(vii) adding to the mixture of step (vi) the bisphosphonate of step (ii);

(viii) incorporating Meroar 73781 as flavouring agent to the mixture of step (vii) once the temperature of the mixture is below 40° C.

(ix) reaching a desired volume with demineralized water; and (x) optionally fractionating the mixture of step (ix).

Example 2

Composition According to the Present Invention Compromising Monosodium Alendronate A composition according to the present invention may comprise the following ingredients with respective amounts:

| | |
|---|---|
| Sodium alendronate | 5.0 mg-140.0 mg |
| Avicel RC591 | 150 mg-500 mg |
| Xanthan gum | 30 mg-100 mg |
| Sorbitol 70% | 3.0 g-15.0 g |
| Sodium saccharine | 10 mg-100 mg |
| Sodium cyclamate | 100 mg-1000 mg |
| Methyl p-hydroxy benzoate | 50 mg-120 mg |
| Propyl p-hydroxy benzoate | 10 mg-30 mg |
| Potassium sorbate | 70 mg-120 mg |
| Orange essence Meroar 73781 | 150 mg-550 mg |
| Sunset yellow (dye) | 1 mg-3 mg |
| Purified water | q.s. 100 ml |

Avicel RC 591 is commercially available by F.M.C. and is comprised of carboxymethylcellulose and microcristalline cellulose.

The composition according to example 1 may be administered daily wherein the content of monosodium alendronate per unit may vary within a range of 5 mg to 20 mg, half-weekly wherein the content of monosodium alendronate per unit may vary within a range of 15 mg to 60 mg, weekly wherein the content may vary in a range of 35 mg to 140 mg, and fortnightly wherein the content may vary in a range of 70 mg to 140 mg.

Example 3

Composition According to the Present Invention Comprising Monosodium Alendronate

| | |
|---|---|
| Sodium alendronate | 5.0 mg-140.0 mg |
| Avicel RC591 | 150 mg-500 mg |
| Xanthan gum | 30 mg-100 mg |
| Sucrose | 10 g-50 g |
| Sorbitol 70% | 3.0 g-15.0 g |
| Methyl p-hydroxy benzoate | 50 mg-120 mg |
| Propyl p-hydroxy benzoate | 10 mg-30 mg |
| Potassium sorbate | 70 mg-120 mg |
| Meroar 73781 | 150 mg:-550 mg |
| Sunset yellow (dye) | 1 mg-3 mg |
| Purified water | q.s. 100 ml |

Example 4

Composition According to the Present Invention Comprising Sodium Olpadronate

| | |
|---|---|
| Sodium olpadronate | 50 mg-600 mg |
| Avicel RC591 | 150 mg-500 mg |
| Xanthan gum | 30 mg-100 mg |
| Sorbitol 70% | 3.0 g-15.0 g |
| Sodium saccharine | 10 mg-100 mg |
| Sodium cyclamate | 100 mg-1000 mg |
| Methyl p-hydroxy benzoate | 50 mg-120 mg |
| Propyl p-hydroxy benzoate | 10 mg-30 mg |
| Potassium sorbate | 70 mg-120 mg |
| Orange essence Meroar 73781 | 150 mg-550 mg |
| Sunset yellow (dye) | 1 mg-3 mg |
| Purified water | q.s. 100 ml |

The composition, according to example 4 may be administered, for example, weekly wherein the content of sodium olpadronate per unit may vary within a range of 50 mg to 500 mg, or fortnightly wherein the content may vary in a range of 100 mg to 500 mg.

Example 5

Composition According to the Present Invention Comprising Sodium Olpadronate

| | |
|---|---|
| Sodium olpadronate | 50 mg-600 mg |
| Avicel RC591 | 150 mg-500 mg |
| Xanthan gum | 30 mg-100 mg |
| Sucrose | 10 g-50 g |
| Sorbitol 70% | 3.0 g-15.0 g |
| Methyl p-hydroxy benzoate | 50 mg-120 mg |
| Propyl p-hydroxy benzoate | 10 mg-30 mg |
| Potassium sorbate | 70 mg-120 mg |
| Orange essence Meroar 73781 | 150 mg-550 mg |
| Sunset yellow (dye) | 1mg-3 mg |
| Purified water | q.s. 100 ml |

Using pamidronate in a composition according to the present invention the amount of pamidronate may be in the range between 50 mg to 600 mg, wherein the remaining ingredients, as already disclosed in the examples, do not change.

As is apparent for persons skilled in the art, other bisphosphonates, as already disclosed in the description, may be used within the present invention.

Moreover, it is possible to use another type of food/soft drink-like beverage, such as another flavouring liquid.

The composition prepared as outlined above may be filled in a one-unit or multi-unit container or commercial kit remarking the modality of medical use, with the aim of preventing incorrect use.

The features disclosed in the description, in the examples and in the claims may, both separately and in any combination thereof, the material for realising the invention in diverse forms thereof. Now that the invention has been described,

What is claimed is:

1. A composition for the oral administration of bisphosphonate to a subject, said composition comprising:
   at least one dissolved bisphosphonate,
   a viscosity agent comprising 5-16.6 parts by weight of a mixture of microcrystalline cellulose plus carboxymethylcellulose and 1 part by weight xanthan gum, wherein microcrystalline cellulose comprises 91.7-86.2% by weight and carboxymethylcellulose 8.3-13.8% by weight of said mixture,
   at least one flavoring agent, and
   purified water,
   wherein said ingredients are formulated such that said composition has the appearance, flavor, and consistency of a fruit juice, and
   wherein said microcrystalline cellulose, carboxymethylcellulose and xanthan gum are present in an amount sufficient to keep the bisphosphonate from precipitation.

2. The composition of claim 1, wherein the bisphosphonate is present in an amount of from about 5 mg to about 600 mg per 100 ml, the viscosity agent is present in an amount from about 30 mg to about 1000 mg per 100 ml, and the flavoring agent is present in an amount from about 150 mg to about 550 mg per 100 ml.

3. The composition of claim 2, wherein said bisphosphonate is sodium alendronate present in an amount of from about 5 mg to about 140 mg per 100 ml.

4. The composition of claim 2, wherein said bisphosphonate is sodium olpadronate present in an amount of from about 5 mg to about 500 mg per 100 ml.

5. The composition of claim 2, wherein said bisphosphonate is disodium pamidronate present in an amount from about 50 mg to about 600 mg per 100 ml.

6. The composition according to claim 1, wherein the flavoring agent confers an orange flavor.

7. A process for preparing the composition comprising (a) at least one dissolved bisphosphonate, (b) a viscosity agent comprising 5-16.6 parts by weight of a mixture of microcrystalline cellulose plus carboxymethylcellulose and part by weight xanthan gum, wherein microcrystalline cellulose comprises about 90% by weight and carboxymethylcellulose about 10% by weight of said mixture, (c) at least one flavoring agent, and (d) purified water, wherein said ingredients are formulated such that said composition has the appearance, flavor, and consistency of a fruit juice, and wherein said microcrystalline cellulose, carboxymethylcellulose and xanthan gum are present in an amount sufficient to keep the bisphosphonate in soluble form, said process comprising:
   (i) suspending said microcrystalline cellulose and said carboxymethylcellulose in a solvent;
   (ii) dissolving said bisphosphonate in demineralized water;
   (iii) separately suspending the xanthan gum in demineralized water;

(iv) homogenizing the carboxymethylcellulose suspension of step (i) into the mixture of step (iii);
(v) adding the mixture of step (iv) to the bisphosphonate mixture of step (ii);
(vi) adding demineralized water to the mixture of step (v) to a predetermined volume; and
(vii) optionally fractionating the mixture of step (vi),
whereby said composition has the appearance, flavor, and consistency of a fruit juice.

8. The process according to claim 7, wherein the bisphosphonate to be dissolved is selected from the group consisting of monosodium alendronate, disodium pamidronate, monosodium olpadronate, amino-alendronate, amino-dimethyl-alendronate, amino-pamidronate, amino-olpadronate, amino-etidronate, neridronate, etidronate, clodronate, ibandronate, incadronate, risedronate, zolendronate, tiludronate, and mixtures thereof.

9. The composition of claim 1, wherein said composition further comprises one or more compounds selected from the group consisting of sorbitol, glycerine, sodium saccharine, sodium cyclamate, methyl p-hydroxy benzoate, propyl p-hydroxybenzoate, sorbic acid, sucrose, and a dye.

10. The process according to claim 7, wherein said bisphosphonate to be dissolved is in a form selected from the group consisting of an acid, a salt, a hydrate, an amino derivative, and a mixture thereof.

11. A method for the administration of bisphosphonate to a subject in need thereof, said method comprising orally administering to said subject in need thereof an effective amount of a composition comprising:
at least one dissolved bisphosphonate,
a viscosity agent comprising 5-16.6 parts by weight of a mixture of microcrystalline cellulose plus carboxymethylcellulose and 1 part by weight xanthan gum, wherein microcrystalline cellulose comprises 91.7-86.2% by weight and carboxymethylcellulose 8.3-13.8% by weight of said mixture,
at least one flavoring agent, and
purified water,
wherein said ingredients are formulated such that said composition has the appearance, flavor, and consistency of a fruit juice, and
wherein said microcrystalline cellulose, carboxymethylcellulose and xanthan gum are present in an amount sufficient to keep the bisphosphonate from precipitation.

12. The method of claim 11, wherein said administration is by pulse administration.

13. The method of claim 11, wherein said subject suffers from or is at risk of a metabolic osteopathy.

14. The method of claim 11, wherein said subject suffers from or is at risk of a cancer metastasis.

15. The method of claim 11, wherein said subject suffers from or is at risk of an osteopathy associated with rheumatoid arthritis.

16. The method of claim 11, wherein said subject suffers from or is at risk of osteoporosis.

17. The method of claim 11, wherein said subject is a child.

18. The method of claim 11, wherein said composition is administered as a pre-breakfast, pre-lunch, or pre-dinner drink.

19. A composition for the oral administration of bisphosphonate to a subject, said composition comprising:
5 mg to about 600 mg of at least one dissolved bisphosphonate,
30 mg to about 1000 mg of a viscosity agent comprising 5-16.6 parts by weight of a mixture of microcrystalline cellulose plus carboxymethylcellulose and 1 part by weight xanthan gum, wherein microcrystalline cellulose comprises 91.7-86.2% by weight and carboxymethylcellulose 8.3-13.8% by weight of said mixture,
150 mg to about 550 mg of at least one flavoring agent, and
purified water to make 100 ml.

* * * * *